(12) United States Patent
Kameya et al.

(10) Patent No.: US 11,453,785 B2
(45) Date of Patent: Sep. 27, 2022

(54) METHOD FOR PRODUCING SURFACE-TREATED COLORED INORGANIC PARTICLES

(71) Applicant: KURARAY NORITAKE DENTAL INC., Kurashiki (JP)

(72) Inventors: Takehiro Kameya, Niigata (JP); Shogo Hiramatsu, Niigata (JP); Masashi Inoue, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 436 days.

(21) Appl. No.: 16/470,661

(22) PCT Filed: Dec. 18, 2017

(86) PCT No.: PCT/JP2017/045395
§ 371 (c)(1),
(2) Date: Jun. 18, 2019

(87) PCT Pub. No.: WO2018/117053
PCT Pub. Date: Jun. 28, 2018

(65) Prior Publication Data
US 2019/0315970 A1 Oct. 17, 2019

(30) Foreign Application Priority Data

Dec. 19, 2016 (JP) .............................. JP2016-245971

(51) Int. Cl.
| | |
|---|---|
| *C09C 3/12* | (2006.01) |
| *A61C 13/00* | (2006.01) |
| *A61C 13/087* | (2006.01) |
| *C08F 20/06* | (2006.01) |
| *C08F 20/18* | (2006.01) |
| *C08F 20/56* | (2006.01) |
| *C09C 3/04* | (2006.01) |
| *C09D 5/02* | (2006.01) |
| *A61K 6/884* | (2020.01) |

(52) U.S. Cl.
CPC ............ *C09C 3/12* (2013.01); *A61C 13/0022* (2013.01); *A61C 13/087* (2013.01); *A61K 6/884* (2020.01); *C08F 20/06* (2013.01); *C08F 20/18* (2013.01); *C08F 20/56* (2013.01); *C09C 3/043* (2013.01); *C09D 5/028* (2013.01); *C01P 2004/61* (2013.01); *C01P 2006/60* (2013.01)

(58) Field of Classification Search
CPC .... A61K 6/884; A61C 13/00; A61C 13/0022; A61C 13/087; C09C 1/24; C09C 1/0081; C09C 1/3081; C09C 1/3684; C09C 3/12; C09D 5/028; C01P 2004/61; C01P 2004/64; C01P 2004/62
USPC .......................................................... 264/13
See application file for complete search history.

(56) References Cited

U.S. PATENT DOCUMENTS

| | | | |
|---|---|---|---|
| 2013/0172441 A1 | 7/2013 | Takahata et al. | |
| 2014/0206792 A1 | 7/2014 | Ishizaka et al. | |
| 2015/0182315 A1 | 7/2015 | Okada et al. | |

FOREIGN PATENT DOCUMENTS

| | | |
|---|---|---|
| EP | 2 604 247 A1 | 6/2013 |
| EP | 2 724 706 A1 | 4/2014 |
| JP | 9-3109 A | 1/1997 |
| JP | 10-36705 A1 | 2/1998 |
| JP | 10-245525 A | 9/1998 |
| JP | 2008-260720 A1 | 10/2008 |
| WO | WO 2012/042911 A1 | 4/2012 |
| WO | WO 2012/176877 A1 | 12/2012 |
| WO | WO 2014/021343 A1 | 2/2014 |

OTHER PUBLICATIONS

Machine Translation of JP 10-36705. (Year: 1998).*
Extended European Search Report dated Jun. 16, 2020 in European Patent Application No. 178849336.0, 6 pages
International Search Report date Jan. 23, 2018, in PCT/JP2017/045395 filed on Dec. 18, 2017.

* cited by examiner

*Primary Examiner* — Hannah J Pak
(74) *Attorney, Agent, or Firm* — Oblon, McClelland, Maier & Neustadt, L.L.P.

(57) ABSTRACT

The present invention provides a method that enables production of a surface-treated colored inorganic particle with which the desired color tone can be consistently reproduced as intended with no variation occurring in the color tone of the compositions produced with the particle, within each production and over multiple production runs. The invention relates to a method for producing a surface-treated colored inorganic particle, comprising spray drying a mixture of a dispersion [I] and a solution [II], wherein the dispersion [I] is a dispersion of inorganic particles having an average particle diameter of 0.005 to 5 μm dispersed in a solvent with a pigment, and the solution [II] is a solution of a surface treatment agent hydrolyzed in the presence of a hydrolysis aid.

15 Claims, No Drawings

METHOD FOR PRODUCING SURFACE-TREATED COLORED INORGANIC PARTICLES

TECHNICAL FIELD

The present invention relates to a method for producing surface-treated colored inorganic particles. Specifically, the invention relates to a method for producing surface-treated colored inorganic particles that includes spray drying a mixture of a dispersion [I] and a solution [II] wherein the dispersion [I] is a dispersion of 0.005- to 5-μm inorganic particles dispersed in a solvent with a pigment, and the solution [II] is a solution of a surface treatment agent hydrolyzed in the presence of a hydrolysis aid.

BACKGROUND ART

Conventionally, the mechanical strength of a composite material produced by polymerizing and curing a paste composition of an inorganic filler and a polymerizable monomer is often improved by hydrophobizing the surface of the inorganic filler with an organic compound, or by treating the surface of the inorganic filler with a silane coupling agent having a polymerizable group.

The method that treats the surface of an inorganic filler with a silane coupling agent is described in, for example, Patent Literature 1, in which 0.005- to 5-μm inorganic particles are dispersed in a solvent, and the inorganic particle dispersion is spray dried after being mixed with a solution of a silane coupling agent hydrolyzed in the presence of a hydrolysis aid. The method produces a surface-treated colorless inorganic particle.

Patent Literature 2 describes a surface-treated colored inorganic particle obtained by mixing surface-treated inorganic particles and a pigment under the wet scheme, and removing the solvent.

CITATION LIST

Patent Literature

Patent Literature 1: JP 10(1998)-36705 A
Patent Literature 2: WO2014/021343

SUMMARY OF INVENTION

Technical Problem

However, a color measurement conducted for polymerized and cured products of paste-like curable compositions obtained in multiple production runs by mixing and kneading surface-treated inorganic particles with a pigment-dispersed polymerizable monomer following Patent Literature 1 revealed that the compositions had color variation to the intended chromaticity, and preferable color tone reproducibility was not obtained.

The same was the case with surface-treated colored inorganic particles obtained following Patent Literature 2. Specifically, color variation occurred to the intended chromaticity, and preferable color tone reproducibility was not obtained in a color measurement conducted for polymerized and cured products of paste-like curable compositions obtained by mixing and kneading the surface-treated colored inorganic particles with a polymerizable monomer in multiple production runs.

The present invention has been made to provide a solution to the problem of the related art, and an object of the present invention is to provide a method that enables production of a surface-treated colored inorganic particle with which the desired color tone reproducibility can be consistently obtained as intended with no variation occurring in the color tone of the compositions produced with the particle, within each production and over multiple production runs. Another object of the invention is to provide a method for producing a paste-like curable composition using the surface-treated colored inorganic particle, and a method for producing a dental mill blank.

Solution to Problem

The present invention relates to the following inventions.
[1] A method for producing a surface-treated colored inorganic particle, comprising spray drying a mixture of a dispersion [I] and a solution [II], wherein the dispersion [I] is a dispersion of inorganic particles having an average particle diameter of 0.005 to 5 μm dispersed in a solvent with a pigment, and the solution [II] is a solution of a surface treatment agent hydrolyzed in the presence of a hydrolysis aid.
[2] The method according to item [1], wherein the surface treatment agent is a silane coupling agent represented by the following general formula (1), $$R^1_n SiX_{4-n}, \qquad (1)$$

wherein $R^1$ is a substituted or unsubstituted hydrocarbon group of 1 to 12 carbon atoms, X represents an alkoxy group of 1 to 4 carbon atoms, an acyloxy group of 1 to 5 carbon atoms, a hydroxyl group, a halogen atom, or a hydrogen atom, and n is an integer of 0 to 3, where $R^1$ may be the same or different when a plurality of $R^1$ exists, and X may be the same or different when a plurality of X exists.
[3] The method according to item [1] or [2], wherein the hydrolysis aid is at least one selected from the group consisting of hydrochloric acid, sulfuric acid, nitric acid, acetic acid, citric acid, malic acid, and lactic acid.
[4] The method according to any one of items [1] to [3], wherein a secondary aggregate of the surface-treated colored inorganic particle after the spray drying has an average particle diameter of 10 to 50 μm.
[5] A method for producing a paste-like curable composition, comprising mixing the surface-treated colored inorganic particle produced by the method of any one of items [1] to [4] with a polymerizable monomer-containing composition comprising a polymerizable monomer and a polymerization initiator.
[6] A method for producing a dental mill blank, comprising polymerizing and curing the paste-like curable composition produced by the method of item [5].
[7] A method for producing a dental mill blank, comprising: contacting a molded product from compression molding of the surface-treated colored inorganic particle produced by the method of any one of items [1] to [4] with a polymerizable monomer-containing composition containing a polymerizable monomer and a polymerization initiator; and polymerizing and curing the polymerizable monomer.

Advantageous Effects of Invention

A surface-treated colored inorganic particle of the present invention is obtained by spray drying a mixture of a dispersion [I] and a solution [II], wherein the dispersion [I] is a dispersion of 0.005 to 5 μm inorganic particles dispersed in a solvent with a pigment, and the solution [II] is a solution of a surface treatment agent hydrolyzed in the presence of a hydrolysis aid. A pigment easily aggregates in a solvent, and it is difficult to control the state of aggregation. The extent of aggregation influences the color tone of the final composition. The color tone deviates from the intended chromaticity as the extent of aggregation increases. The surface-treated colored inorganic particle of the present invention is produced by mixing inorganic particles and a pigment in a solvent, and, by the presence of the inorganic particles between pigment particles, the pigment can be restrained from reaggregation. Reaggregation of pigment particles also can be restrained because the solvent is instantaneously removed at the time of spray drying. Accordingly, the pigment particles are uniformly dispersed between the inorganic particles after drying. That is, the pigment becomes uniformly dispersed in the composition when mixed with a polymerizable monomer in a subsequent step, and, accordingly, the composition having preferably color tone reproducibility to the intended chromaticity can be obtained. Another advantage of the pigment being uniformly dispersed is the improved flexural strength because the pigment, when it aggregates, tends to become an initiation point of fracture in the cured product.

DESCRIPTION OF EMBODIMENTS

A surface-treated colored inorganic particle producing method of the present invention is a method that spray dries a mixture of a dispersion [I] and a solution [II], wherein the dispersion [I] is a dispersion of inorganic particles having an average particle diameter of 0.005 to 5 μm dispersed in a solvent with a pigment, and the solution [II] is a solution of a surface treatment agent hydrolyzed in the presence of a hydrolysis aid.

In this specification, the upper and lower limits of numerical ranges (e.g., contents of components, and calculated values and various properties of components) may be combined as appropriate.

The dispersion [I] is described first. In the present invention, the dispersion [I] is prepared by dispersing inorganic particles and a pigment in a solvent.

The inorganic particles used in the present invention have an average particle diameter of 0.005 to 5 μm, preferably 0.010 to 4.0 μm, more preferably 0.020 to 3.0 μm, even more preferably 0.025 to 2.5 μm. The inorganic particles are not particularly limited, as long as the average particle diameter falls in these ranges. Inorganic particles having an average particle diameter of less than 0.005 μm do not easily disperse, whereas inorganic particles having an average particle diameter of more than 5 μm fail to make a stable dispersion state because inorganic particles in this average particle diameter range settle while being dispersed. The inorganic particles may be the same type of inorganic particle, or two or more kinds of inorganic particles used in combination.

In the specification, the average particle diameter of the inorganic particles can be determined by using a laser diffraction scattering method, or by observing the particles with an electron microscope. Specifically, a laser diffraction scattering method is more convenient for particles of 0.10 μm or more, whereas electron microscopy is a more convenient method of particle diameter measurement when the inorganic particles are ultrafine particles of less than 0.10 μm.

To be more specific about the laser diffraction scattering method, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

To be more specific about electron microscope observation, the average particle diameter can be measured by taking a micrograph of the particles with a transmission electron microscope (Model H-800NA, manufactured by Hitachi, Ltd.) and measuring the particle diameters of (200 or more) particles observed in a unit area field view in the micrograph by the use of an image-analyzing particle size distribution analysis software (MacView, manufactured by Mountech Co., Ltd.). In this case, the particle diameter of each particle is determined as the diameter of a corresponding circle having the same area as the particle, and the average primary particle diameter is calculated from the number of particles and the measured particle diameters.

Known inorganic particles used as filling materials of dental composite resins may be used without any restriction as the inorganic particles used in the present invention. Specific examples of known materials that can be used as the inorganic particles include glass materials (silicon dioxide, such as quartz, fused quartz, and silica gel; and glass containing silicon as a main component, with boron and/or aluminum added to the glass along with various heavy metals), alumina, various ceramics, diatomaceous earth, kaolin, clay minerals (such as montmorillonite), activated earth, synthetic zeolite, mica, silica, calcium fluoride, ytterbium fluoride, calcium phosphate, barium sulfate, zirconium dioxide (zirconia), titanium dioxide (titania), and hydroxyapatite. It is also possible to use organic-inorganic composite particles (organic-inorganic composite fillers) obtained by adding a polymerizable monomer to the inorganic particles, and polymerizing and curing the resulting paste before pulverizing it. The inorganic particles may be used alone, or two or more thereof may be used in combination.

One important property desired for dental restorative materials is radiopacity. When such a property is to be imparted, inorganic oxides having heavy metal elements such as zirconium, barium, titanium, lanthanum, and strontium are used as the inorganic particles.

Examples of inorganic particles having radiopacity include a barium borosilicate glass (for example, E-3000 manufactured by Esstech, Inc.; 8235, GM27884, GM39923 manufactured by Schott AG), a strontium boroaluminosilicate glass (for example, E-4000 manufactured by Esstech, Inc.; G018-093, GM32087 manufactured by Schott AG), a lanthanum glass (for example, GM31684 manufactured by Schott AG), a fluoroaluminosilicate glass (for example, G018-091, G018-117 manufactured by Schott AG), a zirconia-containing glass (for example, G018-310, G018-159 manufactured by Schott AG), a strontium-containing glass (for example, G018-163, G018-093, GM32087 manufactured by Schott AG), a zinc oxide-containing glass (for example, G018-161 manufactured by Schott AG), and a calcium-containing glass (for example, G018-309 manufactured by Schott AG).

The form of the inorganic particles is not particularly limited, and the inorganic particles may have a variety of shapes, including, for example, a crushed shape, a plate shape, a scale shape, a fibrous shape (a short fiber, a long fiber), a stylus shape, a whisker shape, and a spherical shape. The inorganic particles may be an aggregate of primary particles of these and other shapes, or a combination of two or more different shapes. In the present invention, the inorganic particles may be particles that have been shaped into these and other shapes by being subjected to some treatment (for example, pulverization).

The pigment used in the present invention may be any of known pigments used for dental compositions, and these may be used without any restriction, provided that the pigment can disperse in the solvent described below. The pigment may be an inorganic pigment and/or an organic pigment. Examples of the inorganic pigment include chromates such as chrome yellow, zinc yellow, and barium yellow; ferrocyanides such as iron blue; sulfides such as vermilion, cadmium yellow, zinc sulfide, antimony white, and cadmium red; sulfates such as barium sulfate, zinc sulfate, and strontium sulfate; oxides such as zinc white, titanium oxide, iron oxide red (rouge), iron oxide black, iron oxide yellow, and chromium oxide; hydroxides such as aluminum hydroxide; silicates such as calcium silicate and ultramarine; and carbon such as carbon black and graphite. Examples of the organic pigment include nitroso pigments such as naphthol green B, naphthol green Y; nitro pigments such as naphthol S, and lithol fast yellow 2G; insoluble azo pigments such as permanent red 4R, brilliant fast scarlet, hansa yellow, and benzidine yellow; poorly soluble azo pigments such as lithol red, lake red C, and lake red D; soluble azo pigments such as brilliant carmine 6B, permanent red F5R, pigment scarlet 3B, and bordeaux 10B; phthalocyanine pigments such as phthalocyanine blue, phthalocyanine green, and sky blue; basic dye pigments such as rhodamine lake, malachite green lake, and methyl violet lake; and acidic dye pigments such as peacock blue lake, eosin lake, and quinoline yellow lake. These pigments may be used alone or in a combination of two or more, and are appropriately selected according to the color tone intended for the dental mill blank. Preferred as the surface-treated colored inorganic particles of the present invention are, for example, titanium oxide, rouge, iron oxide black, and iron oxide yellow because these inorganic pigments have preferable heat resistance or lightfastness. In the specification, components having the properties of both inorganic particle and pigment can be regarded as pigments when used in small amounts (for example, less than 5 parts by mass, or less than 1 part by mass relative to total 100 parts by mass of the inorganic particle and the pigment) for the purpose of adjusting the color to match the desired color tone, and as inorganic particles when the average particle diameter is 0.005 to 5 μm and when used in large amounts (for example, 1 part by mass or more, 5 parts by mass or more, 10 parts by mass or more, or 30 parts by mass or more relative to total 100 parts by mass of the inorganic particle and the pigment).

The pigment content is appropriately adjusted according to the desired color tone, and is not particularly limited. However, the pigment content is preferably 0.000001 to 5 parts by mass, more preferably 0.00001 to 1 parts by mass relative to 100 parts by mass of the inorganic particles mixed with the pigment.

The solvent used in the present invention is not particularly limited, and can be selected from known solvents, provided that the inorganic particles and the pigment can be dispersed. Preferred examples include water, organic solvents containing a small amount of dissolved water (for example, polar solvents such as methanol, ethanol, propanol, butanol, and acetone, and mixed solvents thereof).

A known homogenizer is used to disperse the inorganic particles and the pigment in a solvent. The homogenizer may be, for example, an immersion homogenizer or an ultrasonic cleaner. The homogenizer may use a mechanical stirrer to stir the solvent in a flow.

The inorganic particles and the pigment may be mixed after being dispersed with a homogenizer in separate containers.

The inorganic particles and the pigment are dispersed in a temperature range that does not cause the solvent to vaporize or solidify, and the temperature is preferably 10 to 60° C., more preferably 20 to 50° C.

The inorganic particles and the solvent are mixed in proportions that produce a slurry. The solvent content is preferably 200 to 1,000 parts by mass, more preferably 300 to 800 parts by mass relative to 100 parts by mass of the inorganic particles.

The dispersion [I] obtained in the manner described above is mixed with a solution [II] (hereinafter referred to also as "hydrolyzed surface treatment agent solution [II]") of a surface treatment agent hydrolyzed in the presence of a hydrolysis aid. The mixture is then spray dried.

The hydrolysis aid is used to bring the solvent pH to 3.5 to 5.5, and may be selected from any known hydrolysis aids without any restriction. Specific examples of the hydrolysis aid include mineral acids such as hydrochloric acid, sulfuric acid, and nitric acid; and carboxylic acids such as acetic acid, citric acid, malic acid, and lactic acid. Preferred are carboxylic acids because carboxylic acids are less likely to remain in the inorganic particles in the subsequent spray drying step. With the solvent pH adjusted to 3.5 to 5.5 (preferably 3.5 to 4.0), the silanol groups (Si—OH) in the surface treatment agent, when it is a silane coupling agent represented by general formula (1) below, gradually condense, and form a siloxane bond (Si—O—Si). This prevents a reactivity loss, and enables the inorganic particle surface to be efficiently treated with silane upon mixing the inorganic particle dispersion [I] with the hydrolyzed surface treatment agent solution [II].

The surface treatment agent may be a known surface treatment agent. Examples of the surface treatment agent include organosilicon compounds; organometallic compounds such as organotitanium compounds, organozirconium compounds, and organoaluminum compounds; and acidic group-containing organic compounds containing at least one acidic group such as a phosphoric acid group, a pyrophosphoric acid group, a thiophosphoric acid group, a phosphonic acid group, a sulfonic acid group, and a carboxylic acid group. Preferred are organosilicon compounds and phosphoric acid group-containing organic compounds. The surface treatment agent may be one of these and other compounds used alone, or two or more of these and other compounds used in combination. When using two or more surface treatment agents in combination, the surface treatment layer may be a mixture of two or more surface treatment agents, or a multilayer structure of more than one surface treatment agent layer. The surface treatment method is not particularly limited, and may be selected from known methods without any restriction.

The organosilicon compounds may be silane coupling agents represented by the following general formula (1).

$$R^1{}_n SiX_{4-n}, \qquad (1)$$

wherein $R^1$ is a substituted or unsubstituted hydrocarbon group of 1 to 12 carbon atoms, X represents an alkoxy group of 1 to 4 carbon atoms, an acyloxy group of 1 to 5 carbon atoms, a hydroxyl group, a halogen atom, or a hydrogen atom, and n is an integer of 0 to 3, where $R^1$ may be the same or different when a plurality of $R^1$ exists, and X may be the same or different when a plurality of X exists. Examples of the hydrocarbon group include alkyl of 1 to 12 carbon atoms, alkenyl of 2 to 12 carbon atoms, and aryl of 6 to 10 carbon atoms. Preferred are alkyl of 1 to 12 carbon atoms. More preferred are alkyl of 1 to 6 carbon atoms. Examples of the alkyl include methyl, ethyl, n-propyl, isopropyl, n-butyl, isobutyl, sec-butyl, 2-methylpropyl, tert-butyl, n-pentyl, isopentyl, sec-pentyl, neopentyl, 1-ethylpropyl, n-hexyl, n-heptyl, n-octyl, n-nonyl, n-decyl, n-undecyl, and n-dodecyl. Examples of the alkenyl include vinyl, allyl, 1-propenyl, 1-methylethenyl, 1-butenyl, 2-butenyl, 3-butenyl, 1-pentenyl, 4-pentenyl, 1-hexenyl, 1-heptenyl, 1-octenyl, 1-nonenyl, 1-decenyl, 1-undecenyl, and 1-dodecenyl. Examples of the aryl include phenyl and naphthyl. Examples of the substituent of the hydrocarbon group include (meth)acryloyloxy, glycidoxy, epoxycycloalkyl of 3 to 6 carbon atoms, hydroxyl, amino, aminoalkyl of 1 to 4 carbon atoms, phenylamino, and a halogen atom. The substituent amino may be substituted with aminoalkyl of 1 to 4 carbon atoms. The number of substituents is preferably 1 to 10, more preferably 1 to 6, even more preferably 1 to 3.

Examples of the C1 to C4 alkoxy representing X include methoxy, ethoxy, n-propoxy, isopropoxy, and n-butoxy. Examples of the C1 to C5 acyloxy representing X include acetoxy, ethylcarbonyloxy, propylcarbonyloxy, isopropylcarbonyloxy, and butylcarbonyloxy.

Examples of the organosilicon compounds include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl tris(2-methoxyethoxy)silane, 3,3,3-trifluoropropyltrimethoxysilane, methyl(3,3,3-trifluoropropyl)dimethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, γ-methacryloyloxypropylmethyldimethoxysilane, 3-methacryloyloxypropylmethyldiethoxysilane, N-2-(aminoethyl)-3-aminopropylmethyldimethoxysilane, N-(2-aminoethyl)-3-aminopropyltrimethoxysilane, N-(2-aminoethyl)-3-aminopropyltriethoxysilane, 3-aminopropyltrimethoxysilane, 3-aminopropyltriethoxysilane, N-phenyl-3-aminopropyltrimethoxysilane, 3-mercaptopropyltrimethoxysilane, trimethylsilanol, methyltrichlorosilane, methyldichlorosilane, dimethyldichlorosilane, trimethylchlorosilane, phenyltrichlorosilane, diphenyklichlorosilane, vinyltrichlorosilane, trimethylbromosilane, diethylsilane, vinyltriacetoxysilane, ω-(meth)acryloyloxyalkyltrimethoxysilane [3 to 12 carbon atoms between the (meth)acryloyloxy group and the silicon atom; e.g., 3-methacryloyloxypropyltrimethoxysilane], and ω-meth)acryloyloxyalkyltriethoxysilane [3 to 12 carbon atoms between the (meth)acryloyloxy group and the silicon atom; e.g., 3-methacryloyloxypropyltriethoxysilane]. As used herein, "(meth)acryloyloxy" is intended to include both methacryloyloxy and acryloyloxy.

Preferred as the silane coupling agent are ones having a functional group that is copolymerizable with a polymerizable monomer. Examples include ω-(meth)acryloyloxyalkyltrimethoxysilane [3 to 12 carbon atoms between the (meth)acryloyloxy group and the silicon atom], ω-(meth)acryloyloxyalkyltriethoxysilane [3 to 12 carbon atoms between the (meth)acryloyloxy group and the silicon atom], vinyltrimethoxysilane, vinyltriethoxysilane, vinyltriacetoxysilane, and 3-glycidoxypropyltrimethoxysilane.

Examples of the organotitanium compounds include tetramethyl titanate, tetraisopropyl titanate, tetra n-butyl titanate, butyl titanate dimers, and tetra(2-ethylhexyl)titanate.

Examples of the organozirconium compounds include zirconium isopropoxide, zirconium n-butoxide, zirconium acetylacetonate, and zirconyl acetate.

Examples of the organoaluminum compounds include aluminum acetylacetonate, and aluminum organic acid salt chelate compounds.

Examples of the phosphoric acid group-containing organic compounds include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxy butyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts thereof.

The acidic group-containing organic compounds having an acidic group such as a pyrophosphoric acid group, a thiophosphoric acid group, a phosphonic acid group, a sulfonic acid group, or a carboxylic acid group may preferably be those recited in, for example, WO2012/042911.

In order to improve the mechanical strength of the cured product by way of improving the chemical bonding between the inorganic particles and a polymerizable monomer, the acidic group-containing organic compounds are more preferably ones having a functional group that is copolymerizable with a polymerizable monomer.

The amount of surface treatment agent is not particularly limited, and is preferably, for example, 0.1 to 50 parts by mass relative to 100 parts by mass of the inorganic particles.

The surface treatment agent used in the present invention is hydrolyzed. The surface treatment agent is subjected to hydrolysis typically by adding a hydrolysis aid to water, or to an organic solvent containing dissolved water. Preferred for use in hydrolysis is water, or an organic solvent containing a small amount of dissolved water (for example, a polar solvent such as methanol, ethanol, propanol, butanol, acetone, or a mixed solvent thereof).

The hydrolysis temperature is not necessarily required to be confined in a specific range, provided that the temperature does not cause the solvent to vaporize or solidify. The hydrolysis temperature is preferably 10 to 60° C., more preferably 20 to 50° C.

The hydrolyzed surface treatment agent solution [II] obtained in the manner described above is mixed with the dispersion [I] of inorganic particles and pigment to obtain a mixture. The mixing conditions are not particularly limited, and these may be mixed, for example, at room temperature (10 to 35° C.).

The mixture can then be spray dried to produce the surface-treated colored inorganic particles. The spray drying temperature is preferably 150 to 300° C., more preferably 170 to 250° C.

The mixture may be spray dried using, for example, a method that sprays the mixture through a nozzle having pores, or a method that uses an atomizer for spray drying whereby the mixture is applied dropwise onto an object rotating at high speed.

Preferably, the inorganic particles obtained after spray drying are further dried, though these particles can directly be used as the surface-treated colored inorganic particles with a composite material. The drying temperature is preferably 80 to 120° C., more preferably 90 to 100° C.

The secondary aggregate of the surface-treated colored inorganic particles obtained after spray drying has an average particle diameter of preferably 10 to 80 μm, more preferably 20 to 60 μm.

The surface-treated colored inorganic particles obtained in the present invention may be used alone or as a mixture of two or more in the paste-like curable composition producing method and the dental mill blank producing method described below. The surface-treated colored inorganic particles may be mixed, for example, by sieving, or by using a rocking mixer or a blender. For example, surface-treated colored inorganic particles having an intermediate color can be produced by taking equal amounts of high-pigment-content surface-treated colored inorganic particles and low-pigment-content surface-treated colored inorganic particles, and mixing these particles using the foregoing method. This makes the procedure easier because it eliminates the need to separately produce surface-treated colored inorganic particles having an intermediate color tone.

Another embodiment of the present invention is a paste-like curable composition producing method that mixes the surface-treated colored inorganic particles produced in the manner described above with a polymerizable monomer-containing composition containing a polymerizable monomer and a polymerization initiator.

The polymerizable monomer-containing composition contains a polymerizable monomer and a polymerization initiator.

The polymerizable monomer used in the present invention is described below. A known polymerizable monomer used in applications such as in dental composite resins and dental cements can be used without any restriction as the polymerizable monomer of the present invention. Typically, radical polymerizable monomers are preferably used. Specific examples of the radical polymerizable monomers include esters such as α-cyanoacrylic acid, (meth)acrylic acid, α-halogenated acrylic acid, crotonic acid, cinnamic acid, sorbic acid, maleic acid, and itaconic acid; (meth)acrylamides; (meth)acrylamide derivatives; vinyl ester compounds; vinyl ether compounds; mono-N-vinyl derivatives; and styrene derivatives. Preferred are (meth)acrylic acid esters, and (meth)acrylamide derivatives, of which (meth)acrylic acid esters are more preferred. As used herein, "(meth)acryl" is intended to include both methacryl and acryl.

Examples of (meth)acrylate polymerizable monomers and (meth)acrylamide derivative polymerizable monomers are as follows.

(i) Monofunctional (meth)acrylates and (meth)acrylamide Derivatives

Examples include methyl(meth)acrylate, isobutyl(meth) acrylate, benzyl(meth)acrylate, lauryl(meth)acrylate, 2-(N, N-dimethylamino)ethyl(meth)acrylate, 2,3-dibromopropyl (meth)acrylate, 2-hydroxyethyl(meth)acrylate, 6-hydroxyhexyl(meth)acrylate, 10-hydroxydecyl(meth) acrylate, propylene glycol mono(meth)acrylate, glyceryl mono(meth)acrylate, erythritol mono(meth)acrylate, N-methylol(meth)acrylamide, N-hydroxyethyl(meth)acrylamide, N-(dihydroxyethyl)(meth)acrylamide, (meth)acryloyloxydodecyl pyridinium bromide, (meth)acryloyloxydodecyl pyridinium chloride, (meth)acryloyloxyhexadecyl pyridinium chloride, (meth)acryloyloxydecyl ammonium chloride, 10-mercaptodecyl(meth)acrylate, 2-(meth)acryloyloxyethyl dihydrogen phosphate, 6-(meth)acryloyloxyhexyl dihydrogen phosphate, 10-methacryloyloxydecyl dihydrogen phosphate, 2-(meth)acryloyloxyethylphenyl hydrogen phosphate, 11-(meth)acryloyloxy-1,1-undecane dicarboxylic acid, 4-[2-(methacryloyloxy)ethoxycarbonyl] phthalic acid anhydrides, and N,N-diethylacrylamide.

(ii) Difunctional (meth)acrylates and (meth)acrylamide Derivatives

Examples include ethylene glycol di(meth)acrylate, triethylene glycol di(meth)acrylate, propylene glycol di(meth) acrylate, neopentyl glycol di(meth)acrylate, 1,6-hexanediol di(meth)acrylate, 1,10-decanediol di(meth)acrylate, 2,2-bis [4-[3-acryloyloxy-2-hydroxypropoxy]phenyl]propane, 2,2-bis[4-[3-methacryloyloxy-2-hydroxypropoxy]phenyl]propane (commonly known as Bis-GMA), 2,2-bis[4-(meth) acryloyloxyethoxyphenyl]propane, 2,2-bis[4-(meth) acryloyloxypolyethoxyphenyl]propane, 1,2-bis[3-(meth) acryloyloxy2-hydroxypropoxy]ethane, pentaerythritol di(meth)acrylate, [2,2,4-trimethylhexamethylene bis(2-carbamoyloxyethyl)]dimethacrylate (commonly known as UDMA), 2,2,3,3,4,4-hexafluoro-1,5-pentyldi(meth)acrylate, N-methacryloyloxyethylacrylamide, bis[2-(meth)acryloyloxyethyl]hydrogen phosphate, and 1,3-dimethacryloyloxypropyl-2-dihydrogen phosphate.

(iii) Tri- and Higher-Functional (meth)acrylates and (meth)acrylamide Derivatives Examples include trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene) bis[2-(aminocarboxy)propane-1,3-diol] tetra (meth)acrylate, 1,7-diacryloyloxy-2,2,6,6-tetraacryloyloxymethyl-4-oxaheptane, and N,N',N'',N'''-tetraacryloyltriethylenetetramine.

Aside from these (meth)acrylic acid ester polymerizable monomers and (meth)acrylamide derivative polymerizable monomers, it is also preferable to use oxirane compounds and oxetane compounds, which can undergo cationic polymerization.

The polymerizable monomer may be any one of these and other polymerizable monomers used alone, or two or more of these and other polymerizable monomers used in combination. The polymerizable monomer used in the present invention preferably has a liquid form. However, the polymerizable monomer is not necessarily required to be liquid, and a solid polymerizable monomer also may be used, provided that it is used in the form of a solution by being mixed with another, liquid polymerizable monomer.

The preferred viscosity range (25° C.) of the polymerizable monomer is 10 Pa·s or less, more preferably 5 Pa·s or less, even more preferably 2 Pa·s or less. However, when two or more polymerizable monomers are used as a solution mixture or by being diluted with a solvent, the individual polymerizable monomers are not necessarily required to satisfy the foregoing viscosity ranges, and more preferably satisfy the foregoing viscosity ranges in the form of a composition prepared for use by mixing and dissolving the polymerizable monomers.

The following describes the polymerization initiator used for polymerization and curing of the polymerizable monomer. The polymerization initiator may be one selected from polymerization initiators commonly used in industry. Preferably, the photopolymerization initiator is one used for dental applications. More preferred are heat polymerization initiators, photopolymerization initiators, and chemical polymerization initiators. The polymerization initiators may be used alone, or two or more thereof may be used in combination.

Examples of the heat polymerization initiators include organic peroxides and azo compounds.

Examples of the organic peroxides include ketone peroxides, hydroperoxides, diacyl peroxides, dialkyl peroxides, peroxyketals, peroxyesters, and peroxydicarbonates.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butyl cumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of the peroxyesters include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleic acid.

Examples of the peroxydicarbonates include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

From a total balance between safety, storage stability, and radical formation potential, the preferred organic peroxides are diacyl peroxides, more preferably benzoyl peroxide.

Examples of the azo compounds include 2,2'-azobis(isobutyronitrile), 2,2'-azobis(2,4-dimethylvaleronitrile), 4,4'-azobis(4-cyanovalaric acid), 1,1'-azobis(1-cyclohexane-1-carbonitrile), dimethyl-2,2'-azobis(isobutyrate), and 2,2'-azobis(2-amidinopropane)dihydrochloride.

Examples of the photopolymerization initiators include (bis)acylphosphine oxides and salts thereof, α-diketones, and coumarins.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, and salts thereof (for example, a sodium salt of 2,4,6-trimethylbenzoylphenylphosphine oxide). Examples of bisacylphosphine oxides include bis(2,6-dichlorobenzoyl)phenylphosphine oxide, bis(2,6dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and salts thereof.

Preferred examples of the (bis)acylphosphine oxides include 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and a sodium salt of 2,4,6-trimethylbenzoylphenylphosphine oxide.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Preferred is camphorquinone.

Examples of the coumarins include the compounds recited in JP 9(1997)-3109 A and JP 10(1998)-245525 A, including 3,3'-carbonylbis(7-diethylaminocoumarin), 3-(4-methoxybenzoyl)coumarin, 3-thienoyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoyl coumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoyl benzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetyl benzo[f]coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho [1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl1H,5H,11H-[1]benzopyrano[6,7,8-ij]quinolizin-11-one, and 10-(2-benzothiazoyl)-2,3,6,7-tetrahydro-1,1,7,7-tetramethyl 1H,5H,11H-[1] benzopyrrano[6,7,8-ij]quinolizin-11-one.

The preferred coumarin compounds are 3,3'-carbonylbis (7-diethylaminocoumarin), and 3,3'-carbonylbis(7-dibutylaminocoumarin).

The photopolymerization initiator is preferably at least one selected from the group consisting of (bis)acylphosphine oxides, α-diketones, and coumarins, which are compounds that are in wide use in the field of dental curable compositions.

Photopolymerization can take place more quickly and efficiently when the photopolymerization initiator is combined with a polymerization accelerator. Accordingly, the polymerizable monomer-containing composition may contain a polymerization accelerator, as needed.

Typical examples of polymerization accelerators preferred for use with the photopolymerization initiator include tertiary amines, aldehydes, thiol group-containing compounds, and sulfinic acid and/or salts thereof.

Examples of the tertiary amines include N,N-dimethylaniline, N,N-dimethylp-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, n-butoxyethyl 4-(N,N-dimethylamino)benzoate, (2-methacryloyloxy)ethyl 4-(N,N-dimethylamino)benzoate, ethyl 4-(N,N-dimethylamino) benzoate, butyl 4-(N,N-dimethylamino)benzoate, N-methyldiethanolamine, 4-(N,N-dimethylamino)benzophenone, trimethylamine, triethylamine, N-methyldiethanolamine, N-ethyldiethanolamine, N-n-butyldiethanolamine, N-lauryldiethanolamine, triethanolamine, 2-(dimethylamino)ethylmethacrylate, N-methyldiethanolamine dimethacrylate, N-ethyldiethanolamine dimethacrylate, triethanolamine monomethacrylate, triethanolamine dimethacrylate, and triethanolamine trimethacrylate.

Examples of the aldehydes include dimethyl aminobenzaldehyde, and terephthalaldehyde. Examples of the thiol group-containing compounds include 2-mercaptobenzooxazole, decanethiol, 3-mercaptopropyltrimethoxysilane, and thiobenzoic acid.

Examples of the sulfinic acid and salts thereof include benzenesulfinic acid, sodium benzenesulfinate, potassium benzenesulfinate, calcium benzenesulfinate, lithium benzenesulfinate, p-toluenesulfinic acid, sodium p-toluenesulfinate, potassium p-toluenesulfinate, calcium p-toluenesulfinate, lithium p-toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4, 6-triethylbenzenesulfinate, calcium 2,4,6-triethylbenzenesulfinate, 2,4,6-triisopropylbenzenesulfinic acid, sodium 2,4,6-trisopropylbenzenesulfinate, potassium 2,4,6-triisopropylbenzenesulfinate, and calcium 2,4,6-trisopropylbenzenesulfinate.

Preferred for use as the chemical polymerization initiators are, for example, organic peroxide-amine redox polymerization initiators, and organic peroxide-amine-sulfinic acid (or a salt thereof) redox polymerization initiators. When a redox polymerization initiator is used, the oxidizing agent and the reducing agent come in separate packages, and these need to be mixed immediately before use. Examples of oxidizing agents of redox polymerization initiators include organic peroxides. The organic peroxide as the oxidizing agent of the redox polymerization initiator is not particularly limited, and known organic peroxides may be used. Specific examples include the organic peroxides exemplified above for the heat polymerization initiators.

From a total balance between safety, storage stability, and radical formation potential, the preferred organic peroxides are diacyl peroxides, more preferably benzoyl peroxide.

The reducing agent of the redox polymerization initiator is typically a tertiary aromatic amine having no electron-withdrawing group in the aromatic ring. Examples of such tertiary aromatic amines having no electron-withdrawing group in the aromatic ring include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis (2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, and N,N-bis(2-hydroxyethyl)-3,5-di-t-butylaniline.

The chemical polymerization initiator may be used with a polymerization accelerator, as needed. The polymerization accelerator used with the chemical polymerization initiator may be one selected from polymerization accelerators commonly used in industry. Preferably, the polymerization accelerator is one used for dental applications. The polymerization accelerators are used alone, or two or more thereof are used in appropriate combination. Specific examples of the polymerization accelerators include amines, sulfinic acid and salts thereof, copper compounds, and tin compounds.

The amines used as polymerization accelerators with the chemical polymerization initiator can be divided into aliphatic amines, and aromatic amines having an electron-withdrawing group in the aromatic ring. Examples of the aliphatic amines include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethylmethacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. From the viewpoint of the curability and storage stability of the composition, tertiary aliphatic amines are preferred, and N-methyldiethanolamine and triethanolamine are more preferred.

As polymerization accelerators used with the chemical polymerization initiator, examples of the tertiary aromatic amines having an electron-withdrawing group in the aromatic ring include ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-N,N-dimethylaminobenzoate, 4-(N,N-dimethylamino) benzophenone, and butyl 4-(N,N-dimethylamino)benzoate. From the viewpoint of imparting preferable curability to the composition, the tertiary aromatic amine having an electron-withdrawing group in the aromatic ring is preferably at least one selected from the group consisting of N,N-bis(2-hydroxyethyl)-p-toluidine, ethyl 4-(N,N-dimethylamino) benzoate, n-butoxyethyl 4-(N,N-dimethylamino) benzoate, and 4-(N,N-dimethylamino)benzophenone.

Examples of the sulfinic acid and salts thereof used as polymerization accelerators include those exemplified above as the polymerization accelerators of the photopolymerization initiator. Preferred are sodium benzenesulfinate, sodium p-toluenesulfinate, and sodium 2,4,6-triisopropylbenzenesulfinate.

Preferred examples of the copper compounds used as polymerization accelerators include copper acetylacetonate, copper(II) acetate, copper oleate, copper(II) chloride, and copper(II) bromide.

Examples of the tin compounds used as polymerization accelerators include di-n-butyl tin dimaleate, di-n-octyl tin dimaleate, di-n-octyl tin dilaurate, and di-n-butyl tin dilaurate. The particularly preferred tin compounds are di-n-octyl tin dilaurate and di-n-butyl tin dilaurate.

The polymerization initiator content is not particularly limited. However, from the viewpoint of the curability and other properties of the composition produced, the polymerization initiator content is preferably 0.001 to 30 parts by mass relative to 100 parts by mass of the polymerizable monomer. With a polymerization initiator content of 0.001 parts by mass or more relative to 100 parts by mass of the polymerizable monomer, polymerization sufficiently proceeds, and there is no fear of reducing mechanical strength. For this reason, the polymerization initiator content is more preferably 0.05 parts by mass or more, even more preferably 0.1 parts by mass or more. With a polymerization initiator content of 30 parts by mass or less relative to 100 parts by mass of the polymerizable monomer, sufficient mechanical strength can be obtained even when the polymerization initiator itself has weak polymerization performance, and there is no fear of causing precipitation from the composition. From this standpoint, the polymerization initiator content is more preferably 20 parts by mass or less.

The method for producing a paste-like curable composition (hereinafter, also referred to simply as "paste") using the surface-treated colored inorganic particle of the present invention is not particularly limited, as long as the method produces a paste-like curable composition of a predetermined color tone containing the surface-treated colored inorganic particle and the polymerizable monomer-containing composition. For example, the method may be (1) a method that includes the step of mixing the surface-treated colored inorganic particle into the polymerizable monomer-containing composition using a biaxial or triaxial kneader, or (2) a method that includes the step of mixing the surface-treated colored inorganic particle into the polymerizable monomer-containing composition using a planetary kneader.

The paste-like curable composition contains the surface-treated colored inorganic particle and the polymerizable monomer-containing composition. The content of the surface-treated colored inorganic particle contained in the paste-like curable composition is typically 40 to 85 mass %, preferably 45 to 80 mass %, more preferably 50 to 75 mass %, though it varies with the diameter or shape of the inorganic particle used. A surface-treated colored inorganic particle content of more than 85 mass % is not suitable because such high contents result in abrupt increase in the viscosity of the paste, and encourage entry of bubbles into the polymer.

Aside from the foregoing components, the paste-like curable composition may contain an additive, for example, such as a pH adjuster, an ultraviolet absorber, an antioxidant, a polymerization inhibitor, a colorant other than pigments, an antimicrobial agent, a radiocontrast agent, a thickener, or a fluorescent agent, depending on the intended use.

Another embodiment of the present invention is a method of production of a dental mill blank using the surface-treated colored inorganic particle. The dental mill blank producing method is not particularly limited, as long as a dental mill blank of a predetermined color tone is obtained that contains the surface-treated colored inorganic particle and a polymer obtained as a cured product of the polymerizable monomer-containing composition containing the polymerizable monomer and the polymerization initiator. The structure of the dental mill blank is not limited to a single color or a single layer, and may have two or more layers. The method may be, for example, (1) a method that includes the step of polymerizing and curing the paste-like curable composition containing the surface-treated colored inorganic particle and the polymerizable monomer-containing composition; (2) a method that includes the steps of obtaining a molding by compression molding of the surface-treated colored inorganic particle charged into a desired mold, and permeating the molding with the polymerizable monomer-containing composition containing the polymerizable monomer and the polymerization initiator, followed by polymerization and curing; or (3) a method that includes the steps of obtaining a molding by compression molding of the surface-treated colored inorganic particle, firing the molding at about 1,000° C. to obtain a porous body, and permeating the porous body with the polymerizable monomer-containing composition containing the polymerizable monomer and the polymerization initiator, followed by polymerization and curing.

The dental mill blank producing method (1) may be, for example, a method in which polymerization and curing is repeated layer by layer until the desired number of layers (two or more layers) is obtained. Specifically, taking a three-layer mill blank as an example, a paste (for example, a first paste) is charged into a mold, and a molded product (for example, a first molded product) is obtained by pressing. Before charging another paste (for example, a second paste) into the mold, the molded product (for example, the first molded product) is polymerized and cured to obtain a cured product, and a new paste (for example, the second paste) is charged onto the cured product, and a molded product (for example, a second molded product) is obtained by pressing. Before charging another paste (for example, a third paste) into the mold, the molded product (for example, the second molded product) is polymerized and cured to obtain a cured product, and a new paste (for example, the third paste) is charged onto the cured product, and a molded product (for example, a third molded product) is obtained by pressing. The molded product (for example, the third molded product) can then be polymerized and cured to obtain the dental mill blank.

The dental mill blank producing method (2) may be a method that includes the steps of layering and compression molding two or more kinds of surface-treated colored inorganic particles to obtain a molding (hereinafter, also referred to as "compression molding step"), and permeating the molding with the polymerizable monomer-containing composition, followed by polymerization and curing. This may be performed using a known method, without any restriction. For example, a method that uniaxially compresses the surface-treated colored inorganic particle with an upper punch and a lower punch after charging the surface-treated colored inorganic particle in a compression mold (die) of the desired size can be conveniently used to obtain the molding. Here, the pressure is typically 10 MPa or more, though an optimum pressure can be appropriately set according to the size of the molded product to be obtained, and the type or diameter of the surface-treated colored inorganic particle. When the pressure is low, it is not possible to densely charge the surface-treated colored inorganic particles, with the result that a sufficiently narrow space cannot be created between the surface-treated colored inorganic particles. In this case, the resulting molded product cannot have a high surface-treated colored inorganic particle content per unit volume. A dental prosthetic appliance produced from such a molded product may suffer from poor mechanical strength or wear resistance, or insufficient surface smoothness and glossiness. It is accordingly preferable from this standpoint to apply as high a pressure as possible. However, considering that production must also take into account factors such as molding size and equipment considerations, the pressure of uniaxial pressing is typically 200 MPa or less, preferably 20 to 100 MPa, more preferably 25 to 80 MPa. The compression time may be appropriately set according to the pressure, and is typically 1 to 120 minutes.

The compression molding in the dental mill blank producing method (2) or (3) is accomplished preferably by cold isostatic pressing (CIP), or a method that incorporates CIP. Specifically, it is preferable to use a method that accomplishes compression molding by CIP without using the uniaxial pressing, or a method in which a molded product after the uniaxial pressing is further subjected to CIP molding. As a rule, CIP molding can accommodate a higher pressure than uniaxial pressing, and enables pressure to be three-dimensionally applied to the molded product in a uniform fashion. With CIP molding, it is thus possible to avoid inclusion of unpreferable micro voids in the molded product, or uneven aggregation of the surface-treated colored inorganic particles. This makes it possible to further increase the compression density of the surface-treated colored inorganic particles, and obtain a dental mill blank having a very high surface-treated colored inorganic particle content. The surface-treated colored inorganic particles may be charged into a highly elastic container (for example, a silicone rubber container or a polyisoprene rubber container), and directly subjected to CIP to obtain a molding, without being compressed by uniaxial pressing in a mold. The applied pressure of CIP molding should preferably be made as high as possible. The CIP machine may be one that can apply a pressure as high as about 1,000 MPa. Examples of such CIP machines include a WET CIP machine, a DRY CIP machine, and a piston-type CIP machine (all manufactured by KOBELCO). Considering productivity and manufacturing cost, the pressure of CIP molding is, for example, 30 to 500 MPa, and the pressure should preferably be increased as high as possible in this range. When productivity is of greater importance, the pressure of CIP molding is, for example, 50 to 500 MPa, preferably 100 to 300 MPa. The CIP molding time may be appropriately set according to the pressure, and is typically 1 to 60 minutes.

The compression molding in the dental mill blank producing method (2) or (3) may be accomplished by, for example, any of the following methods. For example, in the case of a dental mill blank having a three-layer laminate configuration, a first surface-treated colored inorganic particle is charged into a uniaxial compression mold (die) fitted with a lower punch, and, with an upper punch set in the mold, the first surface-treated colored inorganic particle is pressed to obtain a first molding. After removing the upper punch, a second surface-treated colored inorganic particle is charged onto the first molding, and, with the upper punch installed back in the mold, the second surface-treated colored inorganic particle is pressed to obtain a second molding of a two-layer structure. After removing the upper punch, a third surface-treated colored inorganic particle is charged onto the second molding, and, with the upper punch installed back in the mold, the third surface-treated colored inorganic particle is pressed to obtain a molding. The molding removed from the mold after the compression molding is a laminate of the first, second, and third surface-treated colored inorganic particles. The pressure in the compression process may have an appropriately set optimum value that depends on the type or amount of the surface-treated colored inorganic particle used, and the pressure may be the same or different for each layer. In the case of a dental mill blank having a three-layer laminate configuration, the first, second, and third surface-treated colored inorganic particles may be pressed at once after these particles are charged into the mold one after another using the same procedures described above, except that the first and the second surface-treated colored inorganic particles are planarized each time instead of being compressed. Because the laminate can have the desired number of layers with a variety of surface-treated colored inorganic particles chosen according to the number of layers, a four-layer laminate can be obtained with four kinds of surface-treated colored inorganic particles in the manner described above. Each constituent layer (for example, the uppermost layer) of the laminate may contain two or more kinds of surface-treated colored inorganic particles.

After these procedures, a molding is obtained that includes at least one layer of surface-treated colored inorganic particles and in which each surface-treated colored inorganic particle layer has a different color tone (hereinafter, also referred to as "surface-treated colored inorganic particle molding" or "compression molded product of surface-treated colored inorganic particles"). The size of the molding is not particularly limited because it can be worked into dental mill blanks of different shapes. In the present invention, the compression molded product of surface-treated colored inorganic particles may be a molding produced by subjecting the surface-treated colored inorganic particles to compression molding at once, or a molding obtained after the compression molding of a laminate produced by separately molding and layering the surface-treated colored inorganic particles, or a molding obtained after the compression molding of surface-treated colored inorganic particles newly molded on the previously formed molding.

The compression molded product of surface-treated colored inorganic particles obtained in the manner described above is then brought into contact with the polymerizable monomer-containing composition. Upon the compression molded product of surface-treated colored inorganic particles contacting the polymerizable monomer-containing composition, the polymerizable monomer enters the spaces between the powdery primary particles, and, as a result, the molded product can have a structure in which the surface-treated colored inorganic particles are very densely distributed in the polymerizable monomer.

The method of contacting the polymerizable monomer-containing composition with the compression molded product of surface-treated colored inorganic particles is not particularly limited, as long as the polymerizable monomer-containing composition can enter the spaces between the surface-treated colored inorganic particles in the molding. The most convenient and preferred method is to immerse the compression molded product of surface-treated colored inorganic particles in the polymerizable monomer-containing composition. With the compression molded product immersed in the polymerizable monomer-containing composition, the polymerizable monomer can gradually permeate into the molded product by capillary action. Preferably, the molded product is immersed under a reduced pressure atmosphere because it facilitates permeation of the liquid-form polymerizable monomer. It is also effective to bring the pressure to reduced pressure and the reduced pressure back to ordinary pressure in a repeated fashion because, by repeating this procedure more than once, the time to completely permeate the molded product with the polymerizable monomer can be reduced. The extent of reduced pressure is appropriately selected according to the viscosity of the polymerizable monomer or the size of inorganic particles. Typically, the pressure is reduced to 100 hectopascal or less, preferably 0.001 to 50 hectopascal, more preferably 0.1 to 20 hectopascal.

As an example of the method of immersing the molded product, the compression molded product of surface-treated colored inorganic particles is placed in a vacuum packing bag containing the polymerizable monomer-containing composition, and the bag is sealed in a reduced pressure environment by being subjected to a predetermined pressure for a predetermined time period using a vacuum packing machine. In this way, the polymerizable monomer-containing composition can isotropically contact the compression molded product of surface-treated colored inorganic particles. This increases the permeation rate, and the time to complete the contact step can be reduced. The extent of reduced pressure in the reduced pressure environment is typically 100 hectopascal or less, preferably 0.001 to 50 hectopascal, more preferably 0.1 to 20 hectopascal. The vacuum packing time is preferably 30 seconds to 20 minutes, more preferably 1 to 10 minutes.

Aside from the immersion method, it is also possible to use a method in which the polymerizable monomer-containing composition is sent into the compression molded product of surface-treated colored inorganic particles in a mold under applied pressure while the surface-treated colored inorganic particles are being compression molded in the mold. In this way, the polymerization and curing step can be continuously carried out in the mold after this process.

The viscosity of the polymerizable monomer-containing composition influences the permeation rate, and permeation typically proceeds at a faster rate with lower viscosities. The preferred viscosity range (25° C.) is 10 Pa·s or less, more preferably 5 Pa·s or less, even more preferably 2 Pa·s or less. The polymerizable monomer needs to be selected taking into account mechanical strength or refractive index, aside from viscosity. The polymerizable monomer-containing composition may be diluted with solvent, and the solvent may be removed in a later pressure-reducing step. It is also possible to speed up the permeation by lowering the viscosity of the polymerizable monomer-containing composition by way of increasing the temperature.

The contact time of the polymerizable monomer-containing composition with the compression molded product of surface-treated colored inorganic particles may be appropriately adjusted according to factors such as the type of surface-treated colored inorganic particle, the size of the molded product, and the extent of monomer permeation. For example, when contact is accomplished by immersion, the contact time is typically 1 to 120 hours. In the case of immersion under reduced pressure, the contact time is typically 0.5 to 12 hours. In a more preferred method of permeating the compression molded product of surface-treated colored inorganic particles with the polymerizable monomer without leaving spaces, a compression molded product of surface-treated colored inorganic particles that appears to have been impregnated with the polymerizable monomer is placed under an applied pressure condition for a certain length of time. That is, the compression molded product of surface-treated colored inorganic particles impregnated with the polymerizable monomer is preferably placed under an applied pressure condition with the polymerizable monomer using, for example, a CIP machine. The applied pressure condition is preferably 20 MPa or more, more preferably 50 MPa or more, even more preferably 100 MPa or more. Even more preferably, the pressure is applied in a repeated fashion by releasing the applied pressure and increasing the pressure from ordinary pressure.

The dental mill blank producing method (3) may be a method that includes the steps of compression molding the surface-treated colored inorganic particles to obtain a molding; firing the molding to produce a porous body; and permeating the porous body with the polymerizable monomer-containing composition, followed by polymerization and curing. This may be performed using a known method, without any restriction. The compression molded product may be obtained in the same manner as in the method (2) described above.

The molding after the compression molding is fired to produce a porous body. The fire temperature is preferably about 1,000 to about 1,300° C., more preferably 1,050 to 1,200° C. The fire time is preferably 1 to 8 hours, more preferably 2 to 4 hours. In this way, the inorganic fillers in the molding partially bind to one another to produce a porous body of a network structure. The pore (diameter) size of the porous body is not particularly limited, and the porous body can have an appropriately selected pore size that varies with various conditions, including the average particle diameter, and the type and amount of the surface-treated colored inorganic particle used, and the fire conditions. For example, the pore size may be about 1 μm to about 20 μm.

The porous body is then subjected to a surface treatment that improves the compatibility of the porous body with the polymerizable monomer-containing composition, using a surface treatment agent. The surface treatment agent may be the same surface treatment agent used for the surface-treated colored inorganic particle, and, preferably, an organosilicon compound is used. As an example, the surface treatment may be performed by immersing the porous body in a mixed solution of ethanol (100 parts by mass), water (5 parts by mass), acetic acid (0.2 parts by mass), and γ-methacryloyloxypropylmethoxysilane (1 part by mass) for 1 hour, and drying the porous body in a vacuum at 90° C. for 3 hours after taking the porous body out of the solution.

The porous body after the surface treatment (hereinafter, referred to as "surface-treated porous body") is then brought into contact with the polymerizable monomer-containing composition.

The method used to contact the surface-treated porous body with the polymerizable monomer-containing composition is not particularly limited, as long as the method allows the polymerizable monomer-containing composition to enter the voids present in the surface-treated porous body. In the most convenient and preferred method, the surface-treated porous body is immersed in the polymerizable monomer-containing composition. With the surface-treated porous body immersed in the polymerizable monomer-containing composition, the polymerizable monomer can gradually permeate into the surface-treated porous body by capillary action. Preferably, the surface-treated porous body is immersed under a reduced pressure atmosphere because it facilitates permeation of the liquid-form polymerizable monomer. It is also effective to bring the pressure to reduced pressure and the reduced pressure back to ordinary pressure in a repeated fashion because, by repeating this procedure more than once, the time to completely permeate the surface-treated porous body with the polymerizable monomer can be reduced. The extent of reduced pressure is appropriately selected according to the viscosity of the polymerizable monomer or the size of inorganic particles. Typically, the pressure is reduced to 100 hectopascal or less, preferably 0.001 to 50 hectopascal, more preferably 0.1 to 20 hectopascal.

As an example of the method of immersing the surface-treated porous body, the surface-treated porous body is placed in a vacuum packing bag containing the polymerizable monomer-containing composition, and the bag is sealed in a reduced pressure environment by being subjected to a predetermined pressure for a predetermined time period using a vacuum packing machine. In this way, the polymerizable monomer-containing composition can isotropically contact the surface-treated porous body. This increases the permeation rate, and the time to complete the contact step can be reduced. The extent of reduced pressure in the reduced pressure environment is typically 100 hectopascal or less, preferably 0.001 to 50 hectopascal, more preferably 0.1 to 20 hectopascal. The vacuum packing time is preferably 30 seconds to 20 minutes, more preferably 1 to 10 minutes.

This is followed by polymerization of the surface-treated porous body containing the polymerizable monomer.

In all of the dental mill blank producing methods of the present invention above, polymerization and curing may be accomplished by means of heat polymerization, photopolymerization, or chemical polymerization, or two or all of the above, using a known method. Preferred in the present invention is heat polymerization because heat polymerization increases the polymerization rate of the polymerizable monomer, and produces a dental mill blank having improved mechanical strength.

The mechanical strength can further improve via increased polymerization rate when the molded product containing the polymerizable monomer, and the paste-covered molded product and surface-treated porous body are polymerized in an inert atmosphere such as a nitrogen gas atmosphere or in a reduced pressure environment in the polymerization and curing process. For productivity, it is preferable that the molded product impregnated with the polymerizable monomer, and the paste-covered molded product and surface-treated porous body be subjected to polymerization in a vacuum by being packed in, for example, a vacuum pack. In this case, polymerization may be performed under applied heat and pressure using, for example, an autoclave. Here, the molded product, and the paste-covered molded product and surface-treated porous body may be polymerized and cured while pressure is being applied. Such polymerization involving heat and pressure is indeed a preferred polymerization and curing method of the present invention. That is, because the surface-treated colored inorganic particle molding and the surface-treated porous body containing the polymerizable monomer are placed under applied pressure conditions with the polymerizable monomer, the polymerizable monomer is able to enter the micro spaces present in the molded product and in the surface-treated porous body, and no micro bubbles remain in the molded product and the porous body. The mechanical strength can further improve when polymerization is performed under an applied pressure condition. The applied pressure condition is preferably 20 MPa or more, more preferably 50 MPa or more, even more preferably 100 MPa or more. As a rule, the pressure should preferably be increased as high as possible. In practice, however, the pressure is dependent on the capability of the pressurizer used. The pressurizer is, for example, an autoclave, a CIP machine, or a HIP (hot isostatic pressing) pressurizer. The CIP machine may be any of the CIP machines exemplified above. Aside from the heat polymerization that involves increased temperature under an applied pressure condition, it is also possible to adopt photopolymerization or chemical polymerization. In a more preferred pressure polymerization method, the molded product or surface-treated porous body impregnated with the polymerizable monomer is polymerized under applied pressure by CIP after being vacuum sealed in, for example, a plastic bag or a rubber tube. Preferably, the pressure should be increased as high as possible. The preferred pressure is 50 MPa or more, more preferably 200 MPa or more. A particularly preferred polymerization method in terms of increasing the mechanical strength is a method in which the sealed molded product or surface-treated porous body is polymerized under high pressure in a processing chamber of a CIP machine by heating the processing chamber after applying a predetermined pressure. For example, the temperature is increased from room temperature to preferably 80° C. to 180° C. over a time period of about 30 minutes to about 24 hours after applying pressure by CIP at room temperature. The polymerization time and the final temperature are set taking into consideration the decomposition temperature of the polymerization initiator contained in the polymerizable monomer.

Preferably, the polymerization and curing is followed by a heat treatment. In this way, the stress and strain occurring inside the cured product can be relaxed, and possible damage to a dental prosthetic appliance as might occur when cutting a dental prosthetic appliance or when using a dental prosthetic appliance at the clinic can be reduced. The heating temperature is preferably 80 to 150° C. The heating time is preferably 10 to 120 minutes.

A dental mill blank is obtained after the foregoing procedures. The dental mill blank may be cut or machined into the desired size, or the surfaces may be polished, as required.

The inorganic particle content in the dental mill blank obtained in the manner described above is typically 45 mass % or more, preferably 65 to 96 mass %, more preferably 70 to 96 mass %, even more preferably 80 to 95 mass %, particularly preferably 85 to 95 mass %, though the content varies with the size and shape of the surface-treated colored inorganic particles used. Here, the inorganic particle content is a measured value in terms of a residue on ignition of the cured product of the polymerizable monomer-containing composition.

For the measurement of the residue on ignition of the cured product, for example, the cured product is placed in a crucible, and heated at 575° C. for a predetermined time period using an electric furnace to burn off the organic resin component. The residue on ignition can then be calculated by measuring the mass of the remaining inorganic particles. In this method, when the dental mill blank is one obtained from the surface-treated colored inorganic particle subjected to a surface treatment, the surface treatment agent used for the surface treatment is treated as a burned organic resin component in the calculations.

Preferably, the dental mill blank of the present invention is worked into a size accommodated by commercially available dental CAD/CAM systems. Preferably, the dental mill blank has a form of, for example, a rectangular column measuring 40 mm×20 mm×15 mm in size, suitable for making a single-tooth bridge; a rectangular column measuring 17 mm×10 mm×10 mm in size, suitable for making inlays or onlays; a rectangular column measuring 14 mm×18 mm×20 mm in size, suitable for making full crowns; or a disc measuring 100 mm in diameter and 10 to 28 mm in thickness, suitable for making long-span bridges or dentures. However, the dental mill blank is not limited to these sizes.

The foregoing configurations may be combined in various forms, and the present invention encompasses such combinations made within the technical scope of the present invention, provided that the effects of the present invention are obtained.

EXAMPLES

The following describes the present invention in greater detail by way of Examples. It should be noted that the present invention is in no way limited by the following Examples, and various changes may be made by a person with ordinary skill in the art within the technical idea of the present invention.

Production Example 1 of Polymerizable Monomer-Containing Composition

A polymerizable monomer-containing composition (A-1) was prepared by dissolving 0.1 parts by mass of camphorquinone as a photopolymerization initiator in 70 parts by mass of [2,2,4-trimethylhexamethylenebis(2-carbamoyloxyethyl)]dimethacrylate (UDMA) and 30 parts by mass of triethylene glycol dimethacrylate (TEGDMA) (the polymerizable monomer-containing composition had a refractive index of 1.51 as a cured product).

Production Example 2 of Polymerizable Monomer-Containing Composition

A polymerizable monomer-containing composition (A-2) was prepared by dissolving 1.0 part by mass of benzoylperoxide as a heat polymerization initiator in 70 parts by mass of [2,2,4-trimethylhexamethylenebis(2-carbamoyloxyethyl)]dimethacrylate (UDMA) and 30 parts by mass of triethylene glycol dimethacrylate (TEGDMA) (the polymerizable monomer-containing composition had a refractive index of 1.51 as a cured product).

Example 1

100 g of a commercially available ultrafine particle silica (Nippon Aerosil Co., Ltd., Aerosil® OX 50; average primary particle diameter: 0.04 µm; refractive index: 1.46; BET specific surface area: 50 $m^2/g$), and a trace amount of pigments consisting of Japanese Pharmacopoeia titanium oxide, iron oxide black, iron oxide red (rouge), and iron oxide yellow were placed in 400 mL of water (the total amount of pigments: 0.16889 g). These were then dispersed with an ultrasonic cleaner for 1 hour to obtain a dispersion. A hydrolysis solution (pH 4.0) prepared as a stirred mixture of 7 g of 3-methacryloyloxypropyltrimethoxysilane, 5 g of water, and 0.1 g of acetic acid was added to the dispersion, and the mixture was stirred for 1 hour at room temperature. The solution was spray dried at 185° C. using a spray drier (B290, manufactured by BUCHI Corporation), followed by further drying at 90° C. for 3 hours. A surface-treated colored inorganic particle (B-1) was obtained after this surface treatment (the secondary aggregate had an average particle diameter of 30 µm) The surface-treated colored inorganic particle (B-1; 50.0 g) was then weighed into a glass mortar, and mixed with 50.0 g of the polymerizable monomer-containing composition (A-1). The mixture was degassed under reduced pressure conditions to remove bubbles in the paste, and a colored paste was obtained.

Example 2

100 g of a commercially available barium borosilicate glass GM27884, UF2.0 grade (Schott AG; average primary particle diameter: 2.0 µm; refractive index: 1.53), and a trace amount of pigments consisting of Japanese Pharmacopoeia titanium oxide, iron oxide black, iron oxide red (rouge), and iron oxide yellow were placed in 400 mL of water (the total amount of pigments: 0.08859 g). These were then dispersed with an ultrasonic cleaner for 1 hour to obtain a dispersion. A hydrolysis solution (pH 4.0) as a stirred mixture of 2 g of 3-methacryloyloxypropyltrimethoxysilane, 5 g of water, and 0.1 g of acetic acid was added to the dispersion, and the mixture was stirred for 1 hour at room temperature. The solution was spray dried in the same manner as in Example 1 to obtain a surface-treated colored inorganic particle (B-2) (the secondary aggregate had an average particle diameter of 45 µm). The surface-treated colored inorganic particle (B-2; 70.0 g) was then weighed into a glass mortar, and mixed with 30.0 g of the polymerizable monomer-containing composition (A-1). The mixture was degassed under reduced pressure conditions to remove bubbles in the paste, and a colored paste was obtained.

Comparative Example 1

100 g of a commercially available ultrafine particle silica (Nippon Aerosil Co., Ltd., Aerosil® OX 50; average primary particle diameter: 0.04 µm; refractive index: 1.46; BET specific surface area: 50 $m^2/g$) was placed in 400 mL of ethanol, and dispersed with an ultrasonic cleaner for 1 hour to obtain a dispersion. A hydrolysis solution as a stirred mixture of 7 g of 3-methacryloyloxypropyltrimethoxysilane, 5 g of water, and 0.1 g of acetic acid was added to the dispersion, and the mixture was stirred for 1 hour at room temperature. The solvent was then removed from the solution under reduced pressure, and the remaining solid was dried at 90° C. for 3 hours. A surface-treated inorganic particle (C-1) was obtained after this surface treatment. A trace amount of pigments consisting of Japanese Pharmacopoeia titanium oxide, iron oxide black, iron oxide red (rouge), and iron oxide yellow was dispersed in 100 g of polymerizable monomer-containing composition (A-1) (the total amount of pigments: 0.16889 g), using an ultrasonic disperser. A weighed 50.0 g of the pigment dispersion was then mixed with a weighed 50.0 g of the surface-treated inorganic particle (C-1) in a glass mortar. The mixture was degassed under reduced pressure conditions to remove bubbles in the paste, and a colored paste was obtained.

Comparative Example 2

100 g of a commercially available barium borosilicate glass GM27884, UF2.0 grade (Schott AG; average primary particle diameter: 0.20 µm; refractive index: 1.53) was placed in 400 mL of ethanol, and dispersed with an ultrasonic cleaner for 1 hour to obtain a dispersion. A hydrolysis solution as a stirred mixture of 2 g of 3-methacryloyloxypropyltrimethoxysilane, 5 g of water, and 0.1 g of acetic acid was added to the dispersion, and the mixture was stirred for 1 hour at room temperature. The solvent was then removed from the solution under reduced pressure, and the remaining solid was dried at 90° C. for 3 hours. This produced a surface-treated inorganic particle (C-2).

A trace amount of pigments consisting of Japanese Pharmacopoeia titanium oxide, iron oxide black, iron oxide red (rouge), and iron oxide yellow was dispersed in 100 g of polymerizable monomer-containing composition (A-1) (the total amount of pigments: 0.20671 g), using an ultrasonic disperser. A weighed 30.0 g of the pigment dispersion was then mixed with a weighed 70.0 g of the surface-treated inorganic particle (C-2) in a glass mortar. The mixture was degassed under reduced pressure conditions to remove bubbles in the paste, and a colored paste was obtained.

Example 3

11.0 g of the surface-treated colored inorganic particle (B-1) produced in Example 1 was laid over a lower punch rod of a press mold having a rectangular hole measuring 30.0 mm×20.0 mm. After spreading the powder by tapping, the upper punch was placed on the powder, and the powder was compression molded under a surface pressure of 100 MPa using a table pressing machine. The resulting molding was then immersed in the polymerizable monomer-containing composition (A-2). The molding was allowed to stand in the dark for 24 hours at room temperature, and deaerated under reduced pressure while being immersed (under 10 hectopascal for 10 minutes). The molded product, impregnated with the polymerizable monomer, was removed after releasing the reduced pressure. Visual inspection confirmed that the polymerizable monomer had thoroughly permeated the molded product, and no bubbles were observed in the molding. The molded product with the impregnated polymerizable monomer was then placed in a vacuum packing bag, and the bag was sealed after reducing the pressure to 10 hectopascal using a vacuum packing machine. The molding was then left to stand under a 50° C. hot-air drier for 20 hours, and subjected to a heat treatment at 130° C. for 1 hour to obtain a cured product.

Example 4

14.0 g of the surface-treated colored inorganic particle (B-2) produced in Example 2 was laid over a lower punch rod of a press mold having a rectangular hole measuring 30.0 mm×20.0 mm. After spreading the powder by tapping, the upper punch was placed on the powder, and the powder was compression molded under a surface pressure of 100 MPa using a table pressing machine. The resulting molding was then immersed in the polymerizable monomer-containing composition (A-2). The molding was allowed to stand in the dark for 24 hours at room temperature, and deaerated under reduced pressure while being immersed (under 10 hectopascal for 10 minutes). The molded product, impregnated with the polymerizable monomer, was removed after releasing the reduced pressure. Visual inspection confirmed that the polymerizable monomer had thoroughly permeated the molded product, and no bubbles were observed in the molding. The molded product with the impregnated polymerizable monomer was then placed in a vacuum packing bag, and the bag was sealed after reducing the pressure to 10 hectopascal using a vacuum packing machine. The molding was then left to stand under a 50° C. hot-air drier for 20 hours, and subjected to a heat treatment at 130° C. for 1 hour to obtain a cured product.

Comparative Example 3

A weighed trace amount of pigments consisting of Japanese Pharmacopoeia titanium oxide, iron oxide black, iron oxide red (rouge), and iron oxide yellow (the total amount of pigments: 0.16889 g) was added to 100 g of the surface-treated inorganic particle (C-1) produced in Comparative Example 1, and the obtained mixture was stirred in 400 mL of ethanol for 30 minutes. A colored inorganic particle (D-1) was obtained upon removing the solvent from the solution under reduced pressure. 11.0 g of the colored inorganic particle (D-1) was laid over a lower punch rod of a press mold having a rectangular hole measuring 30.0 mm×20.0 mm. After spreading the powder by tapping, the upper punch was placed on the powder, and the powder was compression molded under a surface pressure of 100 MPa using a table pressing machine. The molding was then immersed in the polymerizable monomer-containing composition (A-2). The molding was allowed to stand in the dark for 24 hours at room temperature, and deaerated under reduced pressure while being immersed (under 10 hectopascal for 10 minutes). The molded product, impregnated with the polymerizable monomer, was removed after releasing the reduced pressure. Visual inspection confirmed that the polymerizable monomer had thoroughly permeated the molded product, and no bubbles were observed in the molding. The molded product with the impregnated polymerizable monomer was then placed in a vacuum packing bag, and the bag was sealed after reducing the pressure to 10 hectopascal using a vacuum packing machine. The molding was then left to stand under a 50° C. hot-air drier for 20 hours, and subjected to a heat treatment at 130° C. for 1 hour to obtain a cured product.

Comparative Example 4

A weighed trace amount of pigments consisting of Japanese Pharmacopoeia titanium oxide, iron oxide black, iron oxide red (rouge), and iron oxide yellow (the total amount of pigments: 0.08859 g) was added to 100 g of the surface-treated inorganic particle (C-2) produced in Comparative Example 2, and the obtained mixture was stirred in 400 mL of ethanol for 30 minutes. A colored inorganic particle (D-2) was obtained upon removing the solvent from the solution under reduced pressure. 14.0 g of the colored inorganic particle (D-2) was laid over a lower punch rod of a press mold having a rectangular hole measuring 30.0 mm×20.0 mm. After spreading the powder by tapping, the upper punch was placed on the powder, and the powder was compression molded under a surface pressure of 100 MPa using a table pressing machine. The molding was then immersed in the polymerizable monomer-containing composition (A-2). The molding was allowed to stand in the dark for 24 hours at room temperature, and deaerated under reduced pressure while being immersed (under 10 hectopascal for 10 minutes). The molded product, impregnated with the polymerizable monomer, was removed after releasing the reduced pressure. Visual inspection confirmed that the polymerizable monomer had thoroughly permeated the molded product, and no bubbles were observed in the molding. The molded product with the impregnated polymerizable monomer was then placed in a vacuum packing bag, and the bag was sealed after reducing the pressure to 10 hectopascal using a vacuum packing machine. The molding was then left to stand under a 50° C. hot-air drier for 20 hours, and subjected to a heat treatment at 130° C. for 1 hour to obtain a cured product.

Chromaticity Evaluation

The colored pastes of Examples 1 and 2 and Comparative Examples 1 and 2 were measured for chromaticity, as follows. A disc-shaped test piece (measuring 10 mm in diameter×1.3 mm) was made from each colored paste, and each test piece was polymerized and cured by applying light to both surfaces (for 10 seconds each side), using a dental visible-light irradiator (PenCure 2000, manufactured by Morita MFG. Corp.). A smooth surface of the polymerized and cured product was polished under dry conditions, using a #1500, a #2000, and a #3000 polishing paper, in this order. The chromaticity of the polished surface of the cured disc, 1.2-mm thick, was then measured with a spectrophotometer (Konica Minolta Japan, Model CM-3610d; measurement was made according to condition c of JIS Z 8722: 2009 with D65 illuminant). A total of five colored pastes for producing test pieces were produced for each Example and Comparative Example. Chromaticity data was collected from measurements conducted for these five colored pastes, and the standard deviation was calculated as an index of variation.

The following procedures were used for the chromaticity measurement of the cured products of Examples 3 and 4 and Comparative Examples 3 and 4. A plate-shaped test piece (10 mm×10 mm×1.3 mm) was cut out from each cured product using a diamond cutter, and a smooth surface of each test piece was polished under dry conditions using a #1500, a #2000, and a #3000 polishing paper, in this order. The chromaticity of the polished surface of the cured product, 1.2-mm thick, was then measured with a spectrophotometer (Konica Minolta Japan, Model CM-3610d; measurement was made according to condition c of JIS Z 8722: 2009 with D65 illuminant). The chromaticity measurement was conducted for each of five test pieces cut out from each cured product. The standard deviation was calculated as an index of variation.

Flexural Strength Measurement of Cured Product

The colored pastes of Examples 1 and 2 and Comparative Examples 1 and 2 were measured for flexural strength, as follows.

The colored paste was charged into a stainless-steel mold (dimensions: 2 mm×2 mm×25 mm). Under the contact pressure of two glass slides from above and below, the colored paste was cured by applying light to both surfaces (5 points on each surface, 10 seconds per point), using a dental visible-light irradiator (PenCure 2000, manufactured by Morita MFG. Corp.). A total of 5 cured products were made for each paste, and the cured products were kept in 37° C. distilled water for 24 hours after being removed from the mold. The flexural strength was measured using a universal testing machine (Shimadzu Corporation; Product Code AGI-100) with a 20-mm distance set between fulcrums and a crosshead speed set at 1 mm/min. Here, a mean value of the measured test pieces was calculated as the flexural strength. A flexural strength of 130 MPa or more was considered preferable for the pastes.

The following procedures were used for the flexural strength measurement of the cured products of Examples 3 and 4 and Comparative Examples 3 and 4. A test piece was cut out from the cured product (dimensions; 2 mm×2 mm×25 mm) using a diamond cutter. A total of five test pieces were made for each cured product, and the samples were kept in 37° C. distilled water for 24 hours. The flexural strength was measured using a universal testing machine (Shimadzu Corporation; Product Code AGI-100) with a 10-mm distance set between fulcrums and a crosshead speed set at 1 mm/min. Here, a mean value of the measured test pieces was calculated as the flexural strength. A flexural strength of 200 MPa or more was considered preferable for the cured products.

TABLE 1

|  |  | Example 1 | | | Example 2 | | | Com. Ex. 1 | | | Com. Ex. 2 | | |
| --- | --- | --- | --- | --- | --- | --- | --- | --- | --- | --- | --- | --- | --- |
| Polymerizable monomer-containing composition | A-1 | 50 | | | 30 | | | 50 | | | 30 | | |
|  | A-2 |  | | |  | | |  | | |  | | |
| Surface-treated colored inorganic particle | B-1 | 50 | | |  | | |  | | |  | | |
| (spray dried) | B-2 |  | | | 70 | | |  | | |  | | |
| Surface-treated inorganic particle | C-1 |  | | |  | | | 50 | | |  | | |
|  | C-2 |  | | |  | | |  | | | 70 | | |
| Chromaticity |  | L* | a* | b* | L* | a* | b* | L* | a* | b* | L* | a* | b* |
| Measured chromaticity value | n = 1 | 81.6 | 7.2 | 28.2 | 82.2 | 4.3 | 29.8 | 81.0 | 6.8 | 27.2 | 82.4 | 4.0 | 30.3 |
|  | n = 2 | 81.5 | 7.2 | 28.2 | 82.1 | 4.2 | 29.7 | 80.8 | 7.2 | 28.1 | 81.9 | 4.8 | 31.0 |
|  | n = 3 | 81.5 | 7.2 | 28.1 | 82.2 | 4.2 | 29.8 | 81.2 | 6.5 | 27.1 | 82.3 | 4.0 | 29.9 |
|  | n = 4 | 81.5 | 7.2 | 28.2 | 82.1 | 4.2 | 29.7 | 81.2 | 6.9 | 27.3 | 82.0 | 3.9 | 30.5 |
|  | n = 5 | 81.5 | 7.2 | 28.2 | 82.2 | 4.3 | 29.8 | 81.8 | 7.0 | 28.3 | 83.2 | 4.5 | 29.2 |
|  | SD | 0.1 | 0.0 | 0.0 | 0.1 | 0.1 | 0.1 | 0.4 | 0.3 | 0.6 | 0.5 | 0.4 | 0.7 |
| Flexural strength (MPa) |  | 150 | | | 155 | | | 118 | | | 120 | | |

TABLE 2

|  |  | Example 3 | | | Example 4 | | | Com. Ex. 3 | | | Com. Ex. 4 | | |
|---|---|---|---|---|---|---|---|---|---|---|---|---|---|
| Polymerizable monomer-containing composition | A-1 | | | | | | | | | | | | |
|  | A-2 | 50 | | | 30 | | | 50 | | | 30 | | |
| Surface-treated colored inorganic particle | B-1 | 50 | | | | | | | | | | | |
| (spray dried) | B-2 | | | | 70 | | | | | | | | |
| Surface-treated colored inorganic particle | D-1 | | | | | | | 50 | | | | | |
| (removal under reduced pressure) | D-2 | | | | | | | | | | 70 | | |
| Chromaticity | | L* | a* | b* | L* | a* | b* | L* | a* | b* | L* | a* | b* |
| Measured chromaticity value | n = 1 | 81.6 | 7.2 | 28.2 | 82.1 | 4.3 | 29.7 | 81.0 | 6.8 | 27.2 | 82.4 | 3.9 | 28.8 |
|  | n = 2 | 81.5 | 7.2 | 28.2 | 82.2 | 4.2 | 29.7 | 80.8 | 7.2 | 28.1 | 81.9 | 4.8 | 31.0 |
|  | n = 3 | 81.5 | 7.2 | 28.1 | 82.2 | 4.2 | 29.8 | 81.2 | 6.5 | 27.1 | 82.3 | 4.0 | 29.9 |
|  | n = 4 | 81.6 | 7.2 | 28.2 | 82.1 | 4.3 | 29.7 | 81.2 | 6.6 | 27.2 | 82.3 | 4.2 | 30.5 |
|  | n = 5 | 81.6 | 7.2 | 28.2 | 82.1 | 4.3 | 29.7 | 82.2 | 6.8 | 28.5 | 81.3 | 4.5 | 29.8 |
|  | SD | 0.1 | 0.0 | 0.0 | 0.1 | 0.1 | 0.0 | 0.5 | 0.3 | 0.6 | 0.5 | 0.4 | 0.8 |
| Flexural strength (MPa) | | 230 | | | 270 | | | 190 | | | 230 | | |

As can be seen from a comparison between Example 1 and Comparative Example 1 and between Example 2 and Comparative Example 2, the more preferable color tone reproducibility was obtained and the variation was smaller when the surface-treated colored inorganic particles were used. The flexural strength values were also higher in the Examples.

As can be seen from a comparison between Example 3 and Comparative Example 3 and between Example 4 and Comparative Example 4, the more preferable color tone reproducibility was obtained and the variation was smaller when the surface-treated colored inorganic particles were used. The flexural strength values were also higher in the Examples.

INDUSTRIAL APPLICABILITY

A producing method of the present invention can provide a surface-treated colored inorganic particle having excellent color tone reproducibility to the intended chromaticity. The invention also can provide a method for producing a composition containing such a surface-treated colored inorganic particle, and a method for producing a dental mill blank. Because the pigment is uniformly dispersed, there is no pigment aggregation, which becomes an initiation point of fracture in the cured product. The result is a cured product of preferable properties, including excellent flexural strength.

The invention claimed is:

1. A method for producing a surface-treated colored inorganic particle, the method comprising:
spray drying a mixture of a dispersion [I] and a solution [II],
wherein the dispersion [I] is a dispersion of inorganic particles having an average particle diameter of 0.005 to 5 μm dispersed in a solvent with a pigment, and
the solution [II] is a solution of a surface treatment agent hydrolyzed in the presence of a hydrolysis aid.

2. The method according to claim 1, wherein the surface treatment agent is a silane coupling agent of formula (1):

$$R^1{}_n SiX_{4-n}, \quad (1)$$

wherein $R^1$ is a substituted or unsubstituted hydrocarbon group of 1 to 12 carbon atoms,
X represents an alkoxy group of 1 to 4 carbon atoms, an acyloxy group of 1 to 5 carbon atoms, a hydroxyl group, a halogen atom, or a hydrogen atom, and n is an integer of 0 to 3, and
wherein $R^1$ is optionally the same or different when a plurality of $R^1$ exists, and
X is optionally the same or different when a plurality of X exists.

3. The method according to claim 1, wherein the hydrolysis aid is at least one selected from the group consisting of hydrochloric acid, sulfuric acid, nitric acid, acetic acid, citric acid, malic acid, and lactic acid.

4. The method according to claim 1, wherein a secondary aggregate of the surface-treated colored inorganic particle after the spray drying has an average particle diameter of 10 to 50 μm.

5. A method for producing a paste curable composition, the method comprising:
mixing the surface-treated colored inorganic particle produced by the method of claim 1 with a polymerizable monomer-containing composition comprising a polymerizable monomer and a polymerization initiator.

6. A method for producing a dental mill blank, the method comprising:
polymerizing and curing the paste curable composition produced by the method of claim 5.

7. A method for producing a dental mill blank, the method comprising:
contacting a molded product from compression molding of the surface-treated colored inorganic particle produced by the method of claim 1 with a polymerizable monomer-containing composition comprising a polymerizable monomer and a polymerization initiator; and
polymerizing and curing the polymerizable monomer.

8. The method according to claim 1, wherein the inorganic particles have an average particle diameter of 0.025 to 2.5 μm.

9. The method according to claim 1, wherein the dispersion [I] includes 0.000001 to 5 parts by mass of the pigment relative to 100 parts by mass of the inorganic particles.

10. The method according to claim 1, wherein the pigment comprises at least one selected from the group consisting of titanium oxide, rouge, iron oxide black, and iron oxide yellow.

11. The method according to claim 1, wherein the solvent comprises water.

12. The method according to claim 1, wherein the spray drying is performed at a temperature of 150° C. to 300° C.

13. The method according to claim 1, further comprising:
drying the surface-treated colored inorganic particle after the spray drying at a temperature of 80° C. to 120° C.

14. The method according to claim 1, further comprising, prior to the spray drying:
mixing the inorganic particles, the solvent, and the pigment, thereby obtaining the dispersion [I];
mixing the surface treatment agent, the hydrolysis aid, and water, thereby obtaining the solution [II]; and
mixing the dispersion [I] and the solution [II], thereby obtaining the mixture.

15. The method according to claim 1, further comprising, prior to the spray drying:
mixing the inorganic particles, the solvent, and the pigment with a homogenizer at a temperature of 10° C. to 60° C., thereby obtaining the dispersion [I];
mixing the surface treatment agent, the hydrolysis aid, and water at a temperature of 10° C. to 60° C., thereby obtaining the solution [II]; and
mixing the dispersion [1] and the solution [11] at a temperature of 10° C. to 35° C., thereby obtaining the mixture.

* * * * *